(12) United States Patent
McIntire

(10) Patent No.: US 6,170,137 B1
(45) Date of Patent: Jan. 9, 2001

(54) EMBALMING FLUID DISTRIBUTION TUBE

(76) Inventor: Jerald R. McIntire, 5699 SE. 3rd St., Midwest City, OK (US) 73110-2057

( * ) Notice: Under 35 U.S.C. 154(b), the term of this patent shall be extended for 0 days.

(21) Appl. No.: 09/146,499

(22) Filed: Sep. 3, 1998

(51) Int. Cl.$^7$ ................ A01N 1/00; A61M 25/00
(52) U.S. Cl. ............... 27/24.1; 604/264; 604/523; 604/902
(58) Field of Search .................. 27/21.1, 22.1, 27/24.1, 24.2; 604/264, 523, 525, 543, 902, 910

(56) References Cited

U.S. PATENT DOCUMENTS

| | | | | |
|---|---|---|---|---|
| 193,368 | * | 7/1877 | Griswold | 27/24.1 |
| 1,945,656 | * | 2/1934 | Richards | 27/24.1 |
| 2,072,346 | * | 3/1937 | Smith | 604/264 |
| 2,097,039 | * | 10/1937 | Peterson | 604/264 |
| 2,156,522 | * | 5/1939 | Bowmer | 604/264 |
| 3,426,759 | * | 2/1969 | Smith | 27/24.1 |
| 3,595,241 | * | 7/1971 | Sheridan | 27/24.1 |
| 3,633,585 | * | 1/1972 | McDonald, Jr. | 604/264 |
| 3,885,561 | * | 5/1975 | Cami | 604/264 |
| 5,800,409 | * | 9/1998 | Bruce | 604/264 |
| 6,019,743 | * | 2/2000 | Cole et al. | 604/15 |

* cited by examiner

Primary Examiner—Dennis Ruhl

(57) ABSTRACT

An embalming fluid distribution tube for inserting into a cavity in a limbs of a cadaver formed by the removal of tissue and bones from the limb. The device includes an elongate flexible tube adapted for insertion into a cavity of a cadaver. One end of the flexible tube is designed for fluidly connecting to an embalming fluid reservoir to permit passage of embalming fluid into the lumen of the flexible tube. The flexible tube has a plurality of transverse slits therethrough to permit passage of embalming fluid in the lumen to the exterior surrounding area around the flexible tube.

20 Claims, 2 Drawing Sheets

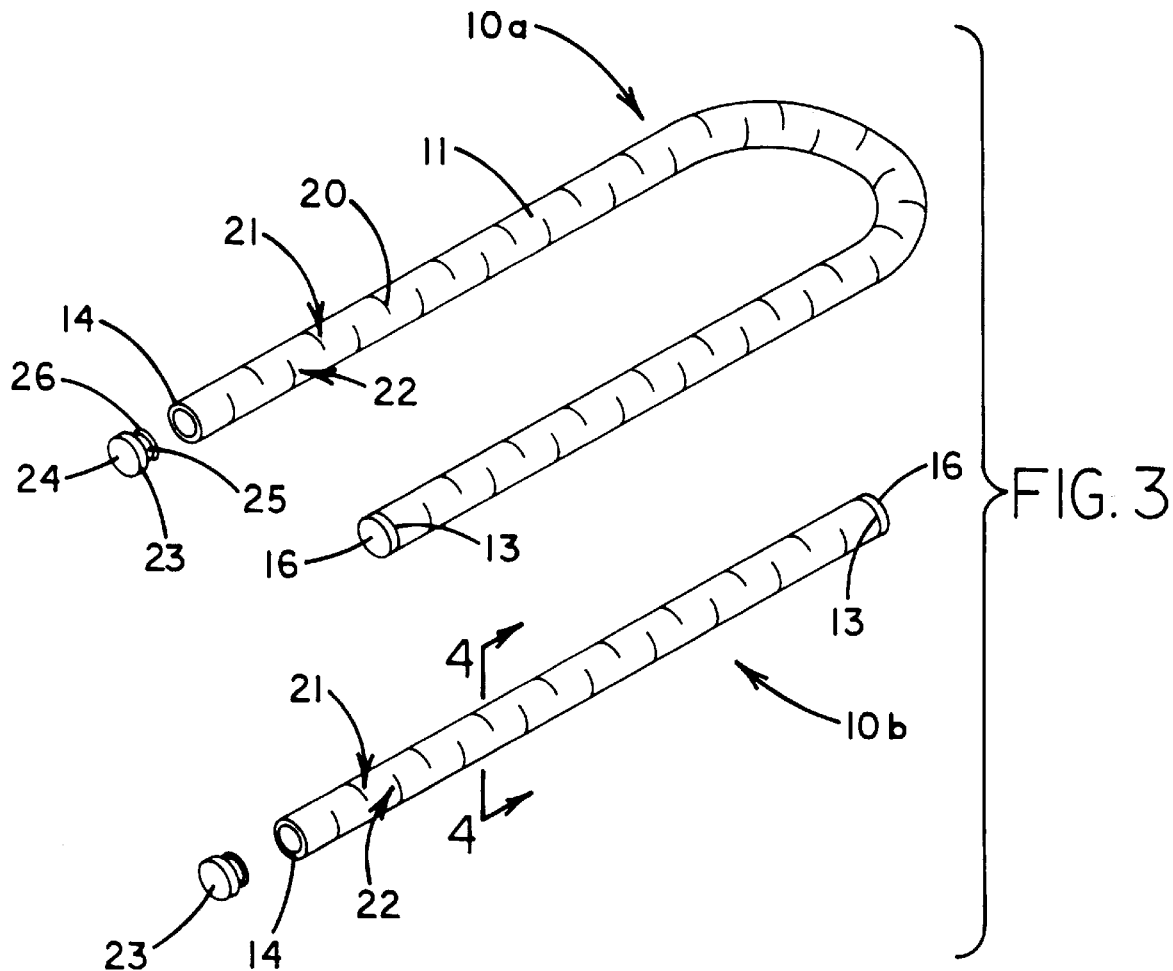
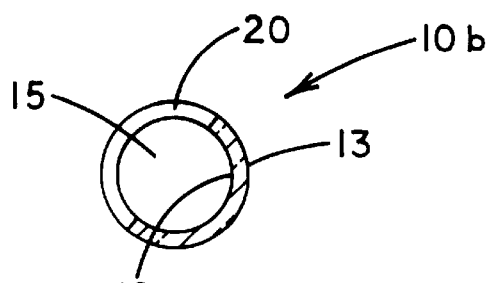

EMBALMING FLUID DISTRIBUTION TUBE

BACKGROUND OF THE INVENTION

1. Field of the Invention

The present invention relates to embalming devices and more particularly pertains to a new embalming fluid distribution tube for inserting into a cavity in a limbs of a cadaver formed by the removal of tissue and bones from the limb.

2. Description of the Prior Art

The use of embalming devices is known in the prior art. More specifically, embalming devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,700,286; U.S. Pat. No. 5,683,462; U.S. Pat. No. 3,514,791; U.S. Pat. No. Des. 375,159; U.S. Pat. No. 3,479,670; and U.S. Pat. No. 3,585,647.

Tissue and bone donor cadavers are a nightmare for funeral homes to prepare for viewing by the family. A lot of extra hard work is needed by the funeral home due to the tissue and bone donation. Even with the best reconstruction, tissue and bone donor cadavers can add several hours to the embalmer's job.

SUMMARY OF THE INVENTION

In view of the foregoing disadvantages inherent in the known types of embalming devices now present in the prior art, the present invention provides a new embalming fluid distribution tube construction wherein the same can be utilized for inserting into a cavity in a limbs of a cadaver formed by the removal of tissue and bones from the limb.

The general purpose of the present invention, which will be described subsequently in greater detail, is to provide a new embalming fluid distribution tube apparatus and method which has many of the advantages of the embalming devices mentioned heretofore and many novel features that result in a new embalming fluid distribution tube which is not anticipated, rendered obvious, suggested, or even implied by any of the prior art embalming devices, either alone or in any combination thereof.

To attain this, the present invention generally comprises an elongate flexible tube adapted for insertion into a cavity of a cadaver. One end of the flexible tube is designed for fluidly connecting to an embalming fluid reservoir to permit passage of embalming fluid into the lumen of the flexible tube. The flexible tube has a plurality of transverse slits therethrough to permit passage of embalming fluid in the lumen to the exterior surrounding area around the flexible tube.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new embalming fluid distribution tube apparatus and method which has many of the advantages of the embalming devices mentioned heretofore and many novel features that result in a new embalming fluid distribution tube which is not anticipated, rendered obvious, suggested, or even implied by any of the prior art embalming devices, either alone or in any combination thereof.

It is another object of the present invention to provide a new embalming fluid distribution tube which may be easily and efficiently manufactured and marketed.

It is a further object of the present invention to provide a new embalming fluid distribution tube which is of a durable and reliable construction.

An even further object of the present invention is to provide a new embalming fluid distribution tube which is susceptible of a low cost of manufacture with regard to both materials and labor, and which accordingly is then susceptible of low prices of sale to the consuming public, thereby making such embalming fluid distribution tube economically available to the buying public.

Still yet another object of the present invention is to provide a new embalming fluid distribution tube which provides in the apparatuses and methods of the prior art some of the advantages thereof, while simultaneously overcoming some of the disadvantages normally associated therewith.

Still another object of the present invention is to provide a new embalming fluid distribution tube for inserting into a cavity in a limbs of a cadaver formed by the removal of tissue and bones from the limb.

Yet another object of the present invention is to provide a new embalming fluid distribution tube which includes an elongate flexible tube adapted for insertion into a cavity of a cadaver. One end of the flexible tube is designed for fluidly connecting to an embalming fluid reservoir to permit passage of embalming fluid into the lumen of the flexible tube. The flexible tube has a plurality of transverse slits therethrough to permit passage of embalming fluid in the lumen to the exterior surrounding area around the flexible tube.

Still yet another object of the present invention is to provide a new embalming fluid distribution tube that allows embalmers a way to quickly and easily restore the appearance of a tissue and bone donor cadaver by delivering embalming fluid directly to the cavities formed by the removed donated tissues and bones.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic perspective view of two different lengths of the present invention.

FIG. 4 is a schematic transverse cross sectional view of the present invention taken from line 4—4 of FIG. 3.

DESCRIPTION OF THE PREFERRED EMBODIMENT

Figure 1:
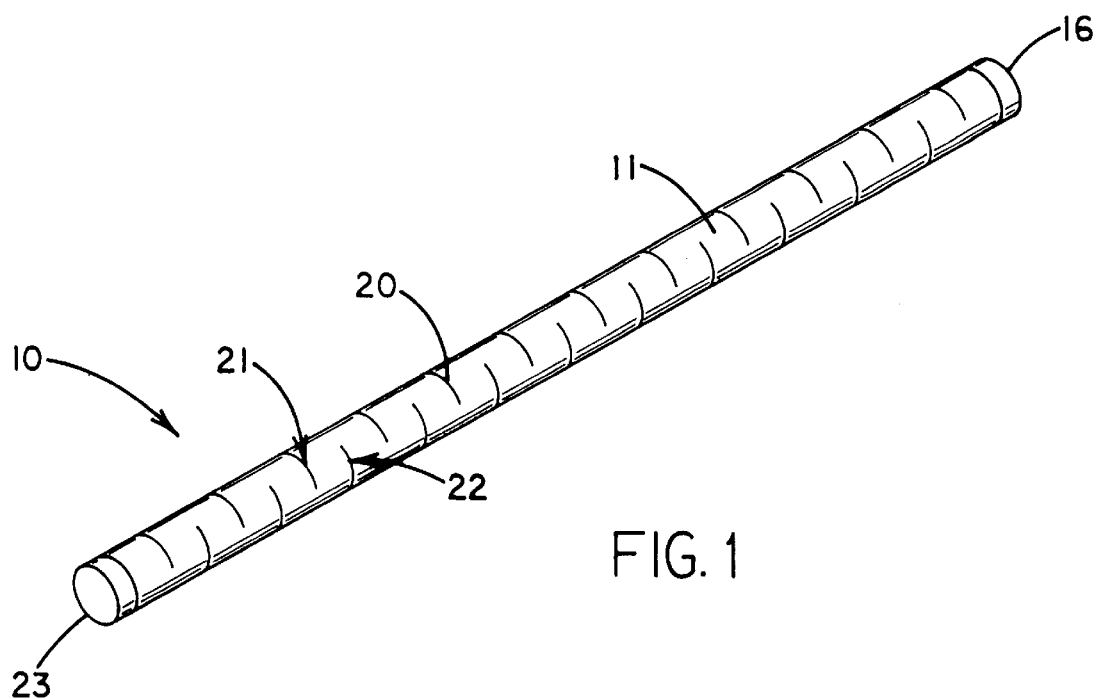
FIG. 1 is a schematic perspective view of a new embalming fluid distribution tube according to the present invention.

With reference now to the drawings, and in particular to FIGS. 1 through 4 thereof, a new embalming fluid distribution tube embodying the principles and concepts of the present invention and generally designated by the reference numeral 10 will be described.

As best illustrated in FIGS. 1 through 4, the embalming fluid distribution tube 10 generally comprises an elongate flexible tube 10 adapted for insertion into a cavity of a cadaver. One end 14 of the flexible tube 10 is designed for fluidly connecting to an embalming fluid reservoir to permit passage of embalming fluid into the lumen 15 of the flexible tube 10. The flexible tube 10 has a plurality of transverse slits 20 therethrough to permit passage of embalming fluid in the lumen 15 to the exterior surrounding area around the flexible tube 10.

In use, the embalming fluid distribution tube 10 is a device for delivering embalming fluid directly to cavities in a cadaver formed by the removal of donor tissues and bones from the cadaver. In closer detail the elongate flexible tube 10 is generally cylindrical and has exterior and interior surfaces 11,12, a pair of opposite ends 13,14, and a longitudinal axis extending between the ends of the flexible tube 10. In use, the flexible tube 10 is designed for insertion into a cavity of a cadaver formed from the removal of tissue and bone from the cadaver. The flexible tube 10 preferably comprises a flexible plastic material so that the flexible tube 10 is flexible in a direction transverse the longitudinal axis of the flexible tube 10 such that the flexible tube 10 may be bent into shapes to conform to the shape of the cavity in the cadaver. The interior surface 12 of the flexible tube 10 defines a lumen 15 of the flexible tube 10. Each of the ends 13,14 of the flexible tube 10 has a generally circular opening into the lumen 15 of the flexible tube 10.

Figure 2:
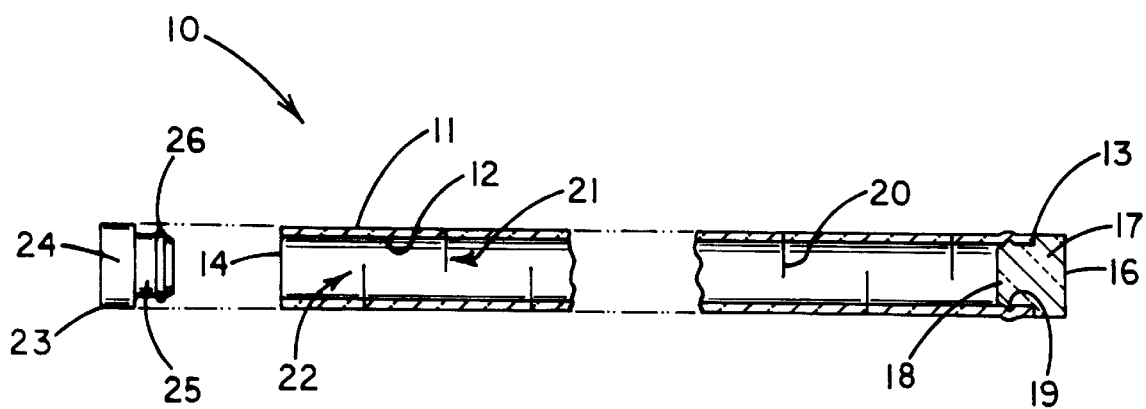
FIG. 2 is a schematic longitudinal cross sectional view of the present invention with the second end cap detached from the second end of the tube.

A first end cap 16 substantially closes the opening of the first end 13 of the flexible tube 10. The first end cap 16 has a head portion 17 and an insertion portion 18. The insertion portion 18 of the first end cap 16 is inserted into the opening of the first end 13 of the flexible tube 10 so that the head portion 17 of the first end cap 16 abuts the first end 13 of the flexible tube. Ideally, the insertion portion 18 of the first end cap 16 is adhesively coupled to the first end 13 of the flexible tube 10 to help insure a water-tight seal between the first end cap 16 and the first end 13 of the flexible tube 10. The flexible tube 10 also ideally comprises a resiliently elastic material to permit resilient stretching of the flexible tube 10 in a radially outwards direction from the longitudinal axis of the flexible tube 10. This allows an outwardly radiating annular ridge 19 around the insertion portion 18 of the first end cap 16. As best illustrated in FIG. 2, the annular ridge 19 of the insertion portion 18 of the first end cap 16 abuts the interior surface 12 of the flexible tube 10 to stretch an adjacent region of the flexible tube 10 to hold the insertion portion 18 of the first end cap 16 to the flexible tube 10.

The second end 14 of the flexible tube 10 is designed for fluidly connecting to the conduit of an embalming fluid reservoir to permit passage of embalming fluid into the lumen 15 of the flexible tube 10.

The flexible tube 10 has a length defined between the ends of the flexible tube 10, the flexible tube 10 has a generally circular cross section has a diameter and a circumference. Preferably, the diameter of the flexible tube 10 is greater than about ⅛ inch. Ideally, the diameter of the flexible tube 10 is about ¼ inch.

The flexible tube 10 has a plurality of transverse slits 20 therethrough between the exterior and interior surfaces 11,12 of the flexible tube 10. The transverse slits 20 are designed for permitting passage of embalming fluid in the lumen 15 to the exterior surrounding area around the flexible tube 10 in the cavity of the cadaver. Each of the transverse slits 20 has a length extending along at least one-fourth of the circumference. Preferably, the lengths of the transverse slits 20 are generally equal to each other. Ideally, each of the transverses slits 20 is generally semi-circular such that the length of each of the transverse slits 20 extends across about one-half of the circumference of the flexible tube 10. Preferably, the transverse slits 20 lie in generally parallel planes to one another generally perpendicular to the longitudinal axis of the flexible tube 10.

The circumference of the flexible tube 10 is divided into first and second semi-circular regions. Preferably, the transverse slits 20 are arranged in a pair of alternating rows 21,22 extending between the ends of the flexible tube 10. One of the rows 21 of transverse slits 20 is located on the first semi-circular region of the circumference of the flexible tube 10 while the other row 22 of transverse slits 20 is located on the second semi-circular region of the circumference of the flexible tube 10 so that there are transverse slits 20 around the entire circumference of the flexible tube 10 to help ensure adequate flow of embalming fluid completely around the flexible tube 10.

The transverse slits 20 are preferably spaced apart at generally equal intervals along the length of the flexible tube 10. Preferably, the interval is greater than about ½ inch. Ideally, the interval is about 1 inch.

With reference to Figure, the tube preferably is made in two distinct lengths. The length of one of the flexible tubes 10a is about 18 inches and has between about 8 and about 10 transverse slits 20. The length of the other flexible tube 10b is about 48 inches and has about 40 transverse slits 20.

Preferably, a second end cap 23 is provided for covering the opening of the second end 14 of the flexible tube 10 when the tube 10 is disconnected from an embalming fluid reservoir. Like the first end cap 16, the second end cap 23 has a head portion 24 and an insertion portion 25. The insertion portion 25 of the second end cap 23 has an outwardly radiating annular ridge 26 therearound. The insertion portion 25 of the second end cap 23 is insertable into the opening of the second end 14 of the flexible tube 10 such that the head portion 24 of the second end cap 23 abuts the second end 14 of the flexible tube 10. The annular ridge of the second end cap 23 abuts the interior surface 12 of the flexible tube 10 when the insertion portion 25 of the second end cap 23 is inserted into the opening of the second end 14 of the flexible tube 10 to stretch an adjacent region of the flexible tube 10 to hold the insertion portion 25 of the second end cap 23 to the flexible tube 10.

In use, the second end of the tube may be inserted into a cadaver with any type of reconstruction device prior to final stitching of the cadaver. For leg cavities, the tube 10a is extended into the leg near the ankle up to the iliac crest area. A short length of the tube is exposed near the iliac crest so that the tube may be fluidly connected by a conduit device to an embalming fluid reservoir. In an arm cavity, the tube 10b is inserted into arm where the proximal humerus was recovered. A short length of the tube is exposed from the proximal humerus and fluidly connected to an embalming fluid reservoir.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An embalming device, comprising:
    an elongate flexible tube having exterior and interior surfaces, a pair of opposite ends, and a longitudinal axis extending between said ends of said flexible tube;
    said flexible tube being adapted for insertion into a cavity of a cadaver;
    said interior surface of said flexible tube defining a lumen of said flexible tube, one of said ends of said flexible tube having an opening into said lumen of said flexible tube;
    said one end of said flexible tube being adapted for fluidly connecting to an embalming fluid reservoir to permit passage of embalming fluid into said lumen of said flexible tube;
    said flexible tube having a plurality of transverse slits therethrough between said exterior and interior surfaces of said flexible tube, said transverse slits being adapted for permitting passage of embalming fluid in said lumen to an exterior surrounding area around the flexible tube;
    further comprising a first end cap, each of said ends of said flexible tube having a generally circular opening into said lumen of said flexible tube, said first end cap substantially closing said opening of a first end of said flexible tube, said first end cap having a head portion and an insertion portion, said insertion portion of said first end cap being inserted into said opening of said first end of said flexible tube, said head portion of said first end cap abutting said first end of said flexible tube; and
    wherein said insertion portion of said first end cap is adhesively coupled to said first end of said flexible tube.

2. The embalming device of claim 1, wherein said flexible tube is generally cylindrical, wherein said flexible tube has a length defined between said ends of said flexible tube, and wherein said flexible tube has a generally circular cross section having a diameter and a circumference.

3. The embalming device of claim 2, wherein each of said transverse slits has a length extending along at least one-fourth of the circumference.

4. The embalming device of claim 3, wherein said lengths of said transverse slits are generally equal to each other.

5. The embalming device of claim 3, wherein said length of each of said transverse slits extends across about one-half of said circumference of said flexible tube.

6. The embalming device of claim 2, wherein said diameter of said flexible tube is greater than about ⅛ inch.

7. The embalming device of claim 2, wherein said length of said flexible tube is about 18 inches and wherein said plurality of transverse slits comprises between about 8 and about 10 transverse slits.

8. The embalming device of claim 2, wherein said length of said flexible tube is about 48 inches and wherein said plurality of transverse slits comprises about 40 transverse slits.

9. The embalming device of claim 1, wherein said transverse slits are spaced apart at generally equal intervals between said ends of said flexible tube.

10. The embalming device of claim 1, wherein said flexible tube comprises a resiliently elastic material to permit resilient stretching of said flexible tube in a radially outwards direction from said longitudinal axis of said flexible tube, and wherein said insertion portion of said first end cap has an outwardly radiating annular ridge therearound, said annular ridge of said insertion portion of said first end cap abutting said interior surface of said flexible tube to stretch an adjacent region of said flexible tube to hold said insertion portion of said first end cap to said flexible tube.

11. An embalming device for delivering embalming fluid directly to cavities in a cadaver formed by the removal of donor tissues and bones from the cadaver, said embalming device comprising:
    an elongate flexible tube being generally cylindrical and having exterior and interior surfaces, a pair of opposite ends, and a longitudinal axis extending between said ends of said flexible tube;
    said flexible tube being adapted for insertion into a cavity of a cadaver;
    wherein said flexible tube comprises a flexible plastic material;
    said interior surface of said flexible tube defining a lumen of said flexible tube, each of said ends of said flexible tube having a generally circular opening into said lumen of said flexible tube;
    a first end cap substantially closing the opening of a first end of said flexible tube, said first end cap having a head portion and an insertion portion, said insertion portion of said first end cap being inserted into said opening of said first end of said flexible tube, said head portion of said first end cap abutting said first end of said flexible tube;

wherein said insertion portion of said first end cap is adhesively coupled to said first end of said flexible tube;

said flexible tube comprising a resiliently elastic material to permit resilient stretching of said flexible tube in a radially outwards direction from said longitudinal axis of said flexible tube;

said insertion portion of said first end cap having an outwardly radiating annular ridge therearound, said annular ridge of said insertion portion of said first end cap abutting said interior surface of said flexible tube to stretch an adjacent region of said flexible tube to hold said insertion portion of said first end cap to said flexible tube;

a second end of said flexible tube being adapted for fluidly connecting to an embalming fluid reservoir to permit passage of embalming fluid into said lumen of said flexible tube;

said flexible tube having a length defined between said ends of said flexible tube, said flexible tube having a generally circular cross section having a diameter and a circumference;

said flexible tube having a plurality of transverse slits therethrough between said exterior and interior surfaces of said flexible tube, said transverse slits being adapted for permitting passage of embalming fluid in said lumen to an exterior surrounding area around the flexible tube;

each of said transverse slits having a length, wherein said lengths of said transverse slits are generally equal to each other, wherein said length of each of said transverse slits extends across about one-half of said circumference of said flexible tube;

said transverse slits lying in generally parallel planes to one another, said planes of said transverse slits being generally perpendicular to said longitudinal axis of said flexible tube;

said circumference of said flexible tube being divided into first and second semi-circular regions, said transverse slits being arranged in a pair of alternating rows extending between said ends of said flexible tube, one of said rows of transverse slits being located on said first semi-circular region of said circumference of said flexible tube, another of said rows of transverse slits being located on said second semi-circular region of said circumference of said flexible tube;

said transverse slits being spaced apart at generally equal intervals along said length of said flexible tube, wherein said interval is greater than about ½ inch;

wherein said diameter of said flexible tube is greater than about ⅛ inch; and a second end cap being adapted for covering the opening of a second end of said flexible tube when said tube is disconnected from an embalming fluid reservoir, said second end cap having a head portion and an insertion portion, said insertion portion of said second end cap having an outwardly radiating annular ridge therearound, said insertion portion of said second end cap being insertable into said opening of said second end of said flexible tube such that said head portion of said second end cap abuts said second end of said flexible tube, said annular ridge of said second end cap abutting said interior surface of said flexible tube when said insertion portion of said second end cap is inserted into said opening of said second end of said flexible tube to stretch an adjacent region of said flexible tube to hold said insertion portion of said second end cap to said flexible tube.

12. An embalming device, comprising:

an elongate flexible tube having exterior and interior surfaces, a pair of opposite ends, and a longitudinal axis extending between said ends of said flexible tube;

said flexible tube being adapted for insertion into a cavity of a cadaver;

said interior surface of said flexible tube defining a lumen of said flexible tube, one of said ends of said flexible tube having an opening into said lumen of said flexible tube;

said one end of said flexible tube being adapted for fluidly connecting to an embalming fluid reservoir to permit passage of embalming fluid into said lumen of said flexible tube;

said flexible tube having a plurality of transverse slits therethrough between said exterior and interior surfaces of said flexible tube, said transverse slits being adapted for permitting passage of embalming fluid in said lumen to an exterior surrounding area around the flexible tube;

further comprising a first end cap, each of said ends of said flexible tube having a generally circular opening into said lumen of said flexible tube, said first end cap substantially closing said opening of a first end of said flexible tube, said first end cap having a head portion and an insertion portion, said insertion portion of said first end cap being inserted into said opening of said first end of said flexible tube, said head portion of said first end cap abutting said first end of said flexible tube; and wherein said flexible tube comprises a resiliently elastic material to permit resilient stretching of said flexible tube in a radially outwards direction from said longitudinal axis of said flexible tube, and wherein said insertion portion of said first end cap has an outwardly radiating annular ridge therearound, said annular ridge of said insertion portion of said first end cap abutting said interior surface of said flexible tube to stretch an adjacent region of said flexible tube to hold said insertion portion of said first end cap to said flexible tube.

13. The embalming device of claim 12, wherein said flexible tube is generally cylindrical, wherein said flexible tube has a length defined between said ends of said flexible tube, and wherein said flexible tube has a generally circular cross section having a diameter and a circumference.

14. The embalming device of claim 13, wherein each of said transverse slits has a length extending along at least one-fourth of the circumference.

15. The embalming device of claim 14, wherein said lengths of said transverse slits are generally equal to each other.

16. The embalming device of claim 14, wherein said length of each of said transverse slits extends across about one-half of said circumference of said flexible tube.

17. The embalming device of claim 13, wherein said diameter of said flexible tube is greater than about ⅛ inch.

18. The embalming device of claim 13, wherein said length of said flexible tube is about 18 inches and wherein said plurality of transverse slits comprises between about 8 and about 10 transverse slits.

19. The embalming device of claim 13, wherein said length of said flexible tube is about 48 inches and wherein said plurality of transverse slits comprises about 40 transverse slits.

20. The embalming device of claim 12, wherein said transverse slits are spaced apart at generally equal intervals between said ends of said flexible tube.

* * * * *